US00RE43580E

(19) United States
(12) Reissued Patent
Stern

(10) Patent Number: US RE43,580 E
(45) **Date of Reissued Patent: *Aug. 14, 2012**

(54) NASAL CALCITONIN FORMULATIONS

(75) Inventor: William Stern, Tenafly, NJ (US)

(73) Assignee: Unigene Laboratories, Inc., Boonton, NJ (US)

( * ) Notice: This patent is subject to a terminal disclaimer.

(21) Appl. No.: 12/459,385

(22) Filed: Jun. 29, 2009

Related U.S. Patent Documents

Reissue of:
(64) Patent No.: 6,440,392
Issued: Aug. 27, 2002
Appl. No.: 09/776,537
Filed: Feb. 2, 2001

U.S. Applications:
(63) Continuation of application No. 10/774,358, filed on Feb. 5, 2004, now Pat. No. Re. 40,812.

(60) Provisional application No. 60/180,241, filed on Feb. 4, 2000.

(51) Int. Cl.
*A61K 9/12* (2006.01)
*A61K 9/00* (2006.01)
*A61K 38/23* (2006.01)

(52) U.S. Cl. ..... 424/43; 424/45; 424/455; 514/2; 514/3; 514/12

(58) Field of Classification Search ..... 424/434, 424/45, 455; 514/2, 3, 12
See application file for complete search history.

(56) References Cited

U.S. PATENT DOCUMENTS

| | | | | |
|---|---|---|---|---|
| 4,151,276 | A | 4/1979 | Caulin et al. | 424/11 |
| 4,476,116 | A | 10/1984 | Anik | |
| 4,609,640 | A | 9/1986 | Morishita et al. | |
| 4,690,952 | A | 9/1987 | Kagatani et al. | 514/11 |
| 4,788,221 | A | 11/1988 | Kagatani et al. | 514/808 |
| 4,845,080 | A | 7/1989 | Fischer | 514/12 |
| 4,900,730 | A | 2/1990 | Miyauchi | 514/12 |
| 5,023,252 | A | 6/1991 | Hseih | 514/183 |
| 5,026,825 | A * | 6/1991 | Grebow et al. | 530/307 |
| 5,059,587 | A | 10/1991 | Yamamoto et al. | 514/12 |
| 5,124,315 | A | 6/1992 | Ceschel et al. | 514/12 |
| 5,169,849 | A | 12/1992 | Kiechel et al. | |
| 5,183,802 | A | 2/1993 | Aliverti et al. | 514/2 |
| 5,234,906 | A | 8/1993 | Young et al. | 514/12 |
| 5,279,836 | A | 1/1994 | Nicolaus | 424/484 |
| 5,281,580 | A | 1/1994 | Yamamoto et al. | 514/12 |
| 5,310,727 | A | 5/1994 | Lattanzi et al. | 514/12 |
| 5,496,801 | A | 3/1996 | Holthuis et al. | 514/12 |
| 5,514,365 | A | 5/1996 | Mardente et al. | 424/45 |
| 5,534,496 | A | 7/1996 | Lee et al. | 514/17 |
| 5,536,508 | A | 7/1996 | Canal et al. | 424/501 |
| 5,571,788 | A | 11/1996 | Arvinte et al. | 514/12 |
| 5,593,962 | A | 1/1997 | Arvinte et al. | 514/12 |
| 5,637,309 | A | 6/1997 | Tajima et al. | 424/423 |
| 5,654,000 | A | 8/1997 | Poli et al. | 424/450 |
| 5,665,700 | A | 9/1997 | Cho et al. | 514/2 |
| 5,693,608 | A | 12/1997 | Bechgaard et al. | 514/2 |
| 5,700,486 | A | 12/1997 | Canal et al. | 424/501 |
| 5,714,477 | A | 2/1998 | Einarsson | 514/56 |
| 5,719,122 | A * | 2/1998 | Chiodini et al. | 514/9 |
| 5,725,871 | A | 3/1998 | Illum | 424/434 |
| 5,726,154 | A | 3/1998 | Baudys et al. | 514/12 |
| 5,733,569 | A | 3/1998 | Azria et al. | |
| 5,733,572 | A | 3/1998 | Unger et al. | 424/450 |
| 5,759,565 | A * | 6/1998 | Azria et al. | 424/434 |
| 5,759,566 | A | 6/1998 | Poli et al. | 424/434 |
| 5,776,886 | A | 7/1998 | Inamoto et al. | 514/2 |
| 5,858,391 | A | 1/1999 | Cuca et al. | 424/439 |
| 5,912,014 | A | 6/1999 | Stern et al. | 424/474 |
| 5,938,654 | A | 8/1999 | Wong et al. | 604/892 |
| 5,968,899 | A | 10/1999 | Sekine et al. | 514/3 |
| 6,008,189 | A | 12/1999 | Inamoto et al. | 514/2 |
| 6,017,538 | A | 1/2000 | Druilhe et al. | 424/191 |
| 6,086,918 | A | 7/2000 | Stern et al. | 424/474 |
| 6,087,338 | A * | 7/2000 | Veronesi et al. | 514/21 |
| 6,107,277 | A | 8/2000 | Veronesi et al. | 514/12 |
| 6,149,893 | A | 11/2000 | Mardente et al. | 424/45 |
| 6,153,582 | A | 11/2000 | Skelnik | 514/12 |
| 6,348,207 | B1 | 2/2002 | Milstein et al. | 424/408 |
| 6,440,392 | B1 | 8/2002 | Stern | 424/43 |

(Continued)

FOREIGN PATENT DOCUMENTS

| | | |
|---|---|---|
| EP | 0 115 627 | 8/1984 |

(Continued)

OTHER PUBLICATIONS

Dua et al, International Journal of Pharmaceutics 147, 1997, pp. 233-242. "The influence of tonicity and viscosity on the intranasal absorption of salmon calcitonin in rabbits".*

(Continued)

*Primary Examiner* — Mina Haghighatian
(74) *Attorney, Agent, or Firm* — Greenberg Traurig, LLP; David J. Dykeman; Danielle T. Abramson

(57) ABSTRACT

[A liquid pharmaceutical composition is disclosed comprising calcitonin or an acid addition salt thereof and citric acid or salt thereof in a concentration from about to about 50 mM, said composition being in a form table for nasal administration.] *A liquid pharmaceutical composition is provided for nasal administration of calcitonin or an acid addition salt thereof. The nasal pharmaceutical formulations contain a component selected from the group consisting of citric acid, citric acid salt and a combination thereof.*

16 Claims, No Drawings

U.S. PATENT DOCUMENTS

| | | | | |
|---|---|---|---|---|
| 6,440,446 | B1 | 8/2002 | Yoshizane et al. | 424/423 |
| 6,447,785 | B1 | 9/2002 | Donovan | 424/239 |
| 6,509,006 | B1 | 1/2003 | Platz et al. | 424/46 |
| RE40,812 | E * | 6/2009 | Stern | 424/434 |

FOREIGN PATENT DOCUMENTS

| | | |
|---|---|---|
| EP | 0 327 756 | 8/1989 |
| EP | 0 358 234 | 3/1990 |
| EP | 0 371 010 | 5/1990 |
| EP | 0 489 217 | 6/1992 |
| EP | 0418697 | * 12/1993 |
| EP | 0 726 075 | 8/1996 |
| EP | 0 809 512 | 12/1997 |
| GB | 2092002 | 8/1982 |
| JP | 05 078258 | 3/1993 |

OTHER PUBLICATIONS

P. Graf et al., Clin.. Exp. Allergy, vol. 25:395-400; 1995 "Benzalkonium chloride in a decongestant nasal spray aggravates rhinitis medicamentosa in healthy volunteers".

H. Hallen et al., Clin. Exp. Allergy, vol. 25:401-405; 1995 "Benzalkonium chloride in nasal decongestive sprays has a long-lasting adverse effect on the nasal mucosa of healthy volunteers".

Berg et al., Laryngoscope 104:1153-1158; 1994 "The Effect of Decongestive Nosedrops on Human Respiratory Mucosa In Vitro".

P.C. Braga et al., J. Pharm. Pharmacol. 44:938-940; 1992 "The effects of calcitonin nsala preparations and their excipients on mucociliary clearance in an ex-vivo frog palate test".

Remington, The Science and Practice of Pharmacy, 20$^{th}$ Edition, Philadelphia (USA) Jan. 2000, Chapter 47, pp. 922-923.

Repertorio Farmaceutico Italiano, REFI 4a Edizione (REFI 4$^{th}$ Edition), 1990, p. A 212, (Calcitonina Spray Nasale Ammour, and p. A223 "Carbicalcin Spray", Farmindustria, Associazione Nazionale dell'Idustria Farmaceutica (National Association of the Pharmaceutical Industry)—CEDOF Editor, 1990.

The Merck Index, 13$^{th}$ Edition, 2001, p. 3576.

Physicians' Desk Reference-PDR 53 Edition 1999, pp. 2057-2059.

Romeijn S.G., et al., Int. J. Pharm.,1996,135/1-2 (137-145), "The Effect of Nasal Drug Formulations on Ciliary Beating in vitro", abstract.

Schipper N.G.M., et al., Calcif. Tissue Int.,1995, 56/4 (280-282), "Methylated (beta)-cyclodextrins are Able to Improve the Nasal Absorption of Salmon Calcitonin", abstract.

Martin E., Pharm. Res., May 1997, 14 (5): 631-7, "Confocal Laser Scanning Microscopic Visualization of the Transport of Dextrans After Nasal Administration to Rats: Effects of Absorption Enhancers", abstract.

Abe K., et al., Chem. Pharm. Bull (Tokyo) Dec. 1995; 43 (12): 2232-7, "Enhanced Nasal Delivery of Luteinizing Hormone Releasing Hormone Agonist Buserelin by Oleic Acid Solubilized and Stabilized in Hydroxypropyl-beta -cyclodextrin", abstract.

Kagatani S., et al., Pharm. Res. 1996 13/5 (739-743), "Enhancement of Nasal Salmon Calcitonin Absorption by Lauroylcarnitine Chloride in Rats", abstract.

Morimoto K., et al., J. Pharma. Pharmacol. 1985 37/2 (134-136) "Enhancement of Nasal Absorption of Insulin and Calcitonin Using Polyacrylic Acid Gel", abstract.

Kurosaki Y., et al., J. Pharmacobiodyn Dec. 1988; 11 (12) : 824-32, "Application of Propranolol to the Keratinized Oral Mucosa: Avoidance of First-Pass Elimination and the Use of 1-Dodecylazacycloheptan-2-one (Azone) as an Absorption Enhancer of Bioadhesive Film-Dosage Form", abstract.

Okamoto H., et al., J. Pharm. Pharmacol Jul. 1987; 39 (7) : 531-4, "Enhanced penetration of mitromycin C through hairless mouse and rats skin by enhancers with terpene moieties", abstract.

Sugibayashi K., et al., J. Pharm. Pharmacol Aug. 1985; 37 (8) : 578-80, "Effect of the Absorption Enhancer, Azone, on the Transport of 5-Fluorouracil Across Hairless Rat Skin", abstract.

Vermehren C., et al., Drug Metab Dispos Sep. 1997; 25 (9): 1083-8, "Absorption and Metabolism of the Absorption Enhancer Didecanoylphosphatidylcholine in Rabbit Nasal Epithelium in vivo", abstract.

Jacobs M.A., et al., Diabetes Nov. 1993; 41 (11) : 1649-55, "The pharmacodynamics and activity of intranasally administered insulin in healthy male volunteers", abstract.

Schipper N.G., et al., Pharm Res Nov. 1996; 13 (11) : 1686-92, "Chitosans as Absorption Enhancers for Poorly Absorbable Drugs. 1: Influence of Molecular Weight and Degree of Acetylation on Drug Transport Across Human Intestinal Epithelial (Caco-2) Cells", abstract.

Pillion D.J., et al., J. Pharm. Sci. Nov. 1995; 84 (11) : 1276-9, "DS-1, A Modified Quillaja Saponin, Enhances Ocula and Nasal Absorption of Insulin", abstract.

Agerholm C., et al., J. Pharm. Sci. Dec. 1994; 83 (12); 1706-11, "Epithelial Transport and Bioavailability of Intranasally Administered Human Growth Hormone Formulated with the Absorption Enhancers Didecanoyl-L-alpha-phosphatidylcholine and alpha-cyclodextrin in Rabbits", abstract.

Critchley H., et al., J. Pharm Pharmacol Aug. 1994; 46 (8) : 651-6, "Nasal Absorption of Desmopressin in Rats and Sheep. Effect of A Bioadhesive Microsphere Delivery System", abstract.

Santus G., et al., Farmaco Dec. 1993; 48 (12) : 1709-33, "Nasal Formulations of Ketorolac Tromethamine: Technological Evaluation—Bioavailability and Tolerability in Rabbits", abstract.

Donovan M.D., et al., Pharm. Res. Aug. 1990; 7 (8) : 808-15, "The Molecular Weight Dependence of Nasal Absorption: the Effect of Absorption Enhancers", abstract.

Pontiroli A.E., et al., Eur J Clin Pharmacol 1989; 37 (4) : 427-30, "Nasal Administration of Glucagon and Human Calcitonin to Healthy Subjects: A Comparison of Powders and Spray Solutions and of Different Enhancing Agents", abstract.

Shao Z., et al., Pharm Res Sep. 1992; 9 (9) : 1157-63, "Cyclodextrins as Nasal Absorption Promoters of Insulin : Mechanistic Evaluations", abstract.

Sarkar M.A., Pharm Res Jan. 1992; 9 (1) : 1-9, "Drug Metabolism in the Nasal Mucosa", abstract.

Morimoto K., et al., Pharm Res Sep. 1991; 8 (9) : 1175-9, "Effects of Proteolytic Enzyme Inhibitors on the Nasal Absorption of Vasopressin and an Analogue", abstract.

Hosoya K., et al., Biol Pharm Bull Feb. 1994; 17 (2) : 316-22,"Evaluation of Enhancers to Increase Nasal Absorption Using Ussing Chamber Technique", abstract.

Tengamnuay P., et al., Pharm Res Apr. 1990; 7 (4) : 370-5, "Bile Salt-Fatty Acid Mixed Micelles as Nasal Absorption Promoters of Peptides. II. In vivo Nasal Absorption of Insulin in Rats and Effects of Mixed Micelles on the Morphological Integrity of the Nasal Mucosa", abstract.

Database WPI, Section Ch, Week 199317, Derwent Publications Ltd., Class 804, AN 1993-140304, XP002300282.

Patent family search for EP 0358234 (equiv. USP 5,026,825),1/34/1 Dialog(R) File 351:Derwent abstract, 008189979, "Intranasal calcitonin formulation—contg. Delta-amino-laevulinic acid for enhanced bioavailability"(priority application 1988).

Patent family search for GB 2212062 (equiv. EP 0327756), 2/34/1 Dialog(R) File 351: Derwent abstract 007943804, "Pharmaceutical Calcitonin—contg. for nasal glycyrrihizinate to enhance mucosal membrane absorption, esp. for nasal administration"(priority application 1987).

Caspar W.R., et al. , Drug & Cosmetic Industry, vol. 156; No. 1; p. 46, "New Ways of Enhancing the Delivery of Skin Care Ingredients", Jan. 1995.

Ratafia, Manny, et al., M&M Medical Marketing & Media, vol. 24; No. 11, p. 10, "Drug Delivery: the Key to Biotechnology Markets", Oct. 1, 1989.

Biotechnology Newswatch, vol. 9, No. 12; p. 1, "Two-nasally delivered CalBio hormones pass initial clinicals", Jun. 19, 1989.

Observations on European Patent Application No. EP 1251867 (third party observations) dated Jan. 17, 2003.

European Search Report dated Oct. 10, 2004.

Database WPI, Section Ch, Week 199317, Derwent Publications Ltd., London , GB; Class B04, AN 1993-140304, XP002300282 & JP 05 078258 A (Suntory) Mar. 30, 1993.
Apotex Notice Letter—Jun. 1, 2006.
Answer to Complaint for Patent Infringement, Affirmative Defenses and Counterclaims, *Unigene Laboratories Inc., et al.* v. *Apotex Inc., et al.*, Civil Action No. 06-CV-5571—RPP-THK, EFC Case (S.D.N.Y.) Sep. 20, 2006.
Declaration of Inventor William Stern Under 37 CFR §1.132 dated Aug. 10, 2005, submitted in parent Reissue U.S. Appl. No. 10/774,358, which reissued as Reissued Patent No. USRE40,812 on Jun. 30, 2009.
Second Declaration of Inventor William Stern Under 37 CFR §1.132 dated Sep. 7, 2007, submitted in parent Reissue U.S. Appl. No. 10/774,358, which reissued as Reissued Patent No. USRE40,812 on Jun. 30, 2009.
Third Declaration of Inventor William Stern under 37 C.F.R. §1.132 dated Oct. 12, 2007, submitted in parent Reissue U.S. Appl. No. 10/774,358, which reissued as Reissued Patent No. USRE40,812 on Jun. 30, 2009.
Fourth Declaration of Inventor William Stern under 37 C.F.R. §1.132 dated Jul. 25, 2008, submitted in parent Reissue U.S. Appl. No. 10/774,358, which reissued as Reissued Patent No. USRE40,812 on Jun. 30, 2009.
Fifth Declaration of Inventor William Stern under 37 C.F.R. §1.132 dated Nov. 17, 2008, submitted in parent Reissue U.S. Appl. No. 10/774,358, which reissued as Reissued Patent No. USRE40,812 on Jun. 30, 2009.
Amended Answer to Complaint for Patent Infringement, Affirmative Defenses and Counterclaims, *Unigene Laboratories Inc., et al.* v. *Apotex Inc., et al.*, Civil Action No. 06-CV-5571—RPP-THK, EFC Case (S.D.N.Y.), May 8, 2007.
Office Action from the European Patent Office concerning European Application Serial No. 01908769.1-1219 dated Feb. 2, 2007.
Jul. 14, 2008 *Hearing Transcript of Unigene Laboratories, Inc., et al.* v. *Apotex, Inc., et al.*, 06 Civ. 5571 (RPP).
Jul. 15, 2008 *Hearing Transcript of Unigene Laboratories, Inc., et al.* v. *Apotex, Inc., et al.*, 06 Civ. 5571 (RPP).
Jul. 16, 2008 *Hearing Transcript of Unigene Laboratories, Inc., et al.* v. *Apotex, Inc., et al.*, 06 Civ. 5571 (RPP).
Opinion and Order dated Aug. 28, 2008 in *Unigene Laboratories, Inc., et al.* v. *Apotex, Inc., et al.*, 06, CV 5571 (RPP).
Declaration of Ashim K. Mitra, Ph.D. Regarding Invalidity of U.S. Patent 6,440,392 dated Oct. 14, 2008 in *Unigene Laboratories, Inc. et al.* v. *Apotex, Inc. et al.*, 06-CV-5571-RPP-THK.
Declaration of Professor Alexander M. Klibanov Regarding Invalidity of U.S. Patent No. 6,440,392 dated Oct. 14, 2008 in *Unigene Laboratories, Inc. et al.* v. *Apotex, Inc. et al.*, 06-CV-5571-RPP-THK.
Declaration of Michael Sofocleous dated Oct. 13, 2008 in *Unigene Laboratories, Inc. et al.* v. *Apotex, Inc. et al.*, 06-CV-5571-RPP-THK.
Declaration of Professor Robert S. Langer Regarding Invalidity of U.S. Patent No. 6,440,392 dated Oct. 14, 2008 in *Unigene Laboratories, Inc. et al.* v. *Apotex, Inc. et al.*, 06-CV-5571-RPP-THK.
Weiner, M., and I.L. Bernstein, 1989, "Adverse Reactions to Drug Formulation Agents", A Handbook of Excipients, Marcel Dekker, Inc. 1989, pp. 361-363 and 390-391.
Stephen G. Farmer, Douglas W.P. Hay, The Airway Epithelium: Physiology, Pathophysiology and Pharmacology, Informa Health Care, 1991: 3-39, Marcel Dekker, Inc.
Akwete Lex Adjei, Pramod K. Gupta, "Inhalation Delivery of Therapeutic Peptides and Proteins", Informa Health Care, 1997:493-514, Marcel Dekker, Inc.
Akers and DeFelippis, Pharmaceutical Formulation Development of Peptides and Proteins, (published 2000), Sven Frokjaer and Lars Hovgaard, Editors Pharmaceutical Fromulation Development of Peptides and Proteins, pp. 145-177, CRC Press 2000.
Expert Report of Henry Kwan, Ph.D. Regarding Validity of U.S. Patent No. 6,440,392, dated Dec. 2, 2008, pp. 1-182.
Expert Report of Dr. Robert P. Raymond, Esq., dated Dec. 2, 2008, pp. 1-23.
Nov. 6, 2007 Hearing Transcript of *Unigene Laboratories, Inc., et al.*, v. *Apotex, Inc., et al.*, 06 CIV 5571 (RPP).
Feb. 4, 2008 Opinion and Order issued in *Unigene Laboratories, Inc., et al.*, v. *Apotex, Inc., et al.*, 06 CIV 5571 (RPP).
Feb. 20, 2008 Defendants' Notice of Motion in Support of Defendants' Motion For Reconsideration of the Feb. 4, 2008 Order Regarding Defendants' Motion to Compel Discovery in *Unigene Laboratories, Inc., et al.* v. *Apotex, Inc., et al.*, 06 CIV 5571 (RPP).
Feb. 20, 2008 Memorandum of Law in Support of Defendants' Motion for Reconsideration of the of the Feb. 4, 2008 Order Regarding Defendants' Motion to Compel Discovery in *Unigene Laboratones, Inc., et al.* v. *Apotex, Inc., et al.*, 06 CIV 5571 (RPP).
Plaintiffs' Memorandum of Law in Opposition to Defendants' Motion for Reconsideration of the Feb. 4, 2008 Order Regarding Defendants' Motion to Comel Discovery in *Unigene Laboratories, Inc., et al.* v. *Apotex, Inc., et al.*, 06 CIV 5571 (RPP).
Feb. 28, 2008 Order issued in *Unigene Laboratories, Inc., et al.*, v. *Apotex, Inc., et al.*, 06 CIV 5571 (RPP).
Armyn P. Sayani, et al. "Systemic Delivery of Peptides and Proteins Across Absorptive Mucoase", Critical Reviews in Therapeutic Drug Carrier Systems, 13 (1&2):85-184 at pp. 106, 127, 128, 144, 158, 160 (1996).
Bell, L.N., "Peptide stability in solids and solutions", Biotechnology Progress 13:342-346. (1997).
Lee, K.C. et al., "Degradation of synthetic salmon calcitonin in aqueous solutions", Pharm. Res. 9:1521-1523. (1992).
Windisch, V. et al., "Degradation Pathways of Salmon Calcitonin in Aqueous Solution", J. Pharm. Sci., 86:359-364. (1997).
M. Gibson, Pharmaceutical Preformulation and Formulation: A Practical Guide from Candidate Drug Selection to Commercial Dosage Form, p. 479 and Chapter 13, Aqueous Nasal Dosage Forms , Ed., Taylor & Francis. (2001).
A.E. Pontiroli, et al., Intranasal calcitonin and plasma calcium concentrations in normal subjects, British Medical Journal, Clinical Research ed., 290:1390-1391. (1985).
P. Nykänen, et al., "Organic acids as excipients in matrix granules for colon-specific drug delivery", Int. J. Pharm. 184:251-261. (1999).
N.R. Anderson, et al., "Quantitative evaluation of pharmaceutical effervescent systems II: Stability monitoring by reactivity and porosity measurements", Journal of Pharmaceutical Sciences, 71:7-13. (1982).
Li, Y., et al., "Effect of a conjugated bile salt on the pulmonary absorption of insulin in rats", Eur. J. Pharm. Biopharm, 39:216-21. (1993).
Kobayashi, S., et al., "Pulmonary delivery of salmon calcitonin dry powders containing absorption enhancers in rats", Pharmaceutical Research, 13:80-83. (1996).
Physicians' Desk Reference 52$^{nd}$ Edition at 1880-1881 (1998).
R.C. Henrikson, et al., Histology, Lippincott Williams and Wilkins pp. 311-321 at 314 (1997).
Pharmaceutical Dosage Forms and Drug Delivery Systems, 7$^{th}$ Edition, Lippincott Williams & Wilkins, pp. 77-81 (1999).
Wade & Weller, Handbook of Pharmaceutical Excipients, 2$^{nd}$ Edition, American Pharmaceutical Association and The Pharmaceutical Press, pp. 34-37, 122-125, 339-345, 439-440 (1994).
D. Voet and J.G. Voet, Biochemistry, 2$^{nd}$ Edition, John Wiley & Sons, New York, pp. 538-541 (1995).
V. Agarwal et al., "Recent trends in drug delivery systems: intranasal drug delivery", Indian Journal of Experimental Biology, 37:6-16. (1999).
D. Harris, et al., "Bioadhesive polymers in peptide drug delivery", Biomaterials, 11:652-658. (1990).
M.J. Cho., et al., "Citric acid as an adjuvant for transepithelial transport", International Journal of Pharmaceutics, 52:79-81. (1989).
Hayashi, et al.., "Physiological mechanism for enhancement of paracellular drug transport", Journal of Controlled Release, 62: 141-148. (1999).
Tyler-Cross et al., "Effects of amino acids sequence, buffers, and ionic strength on the rate and mechanism of deamidation of asparagine residues in small peptides", Journal of Biological Chemistry 266:22549-22556. (1991).

Reubsaet et al., "Degradation kinetics of antagonist [Arg$^{6}$, D-Trp$^{7,9}$, MePhe$^{8}$]-substance P {6-11} in aqueous solutions", Analytical Biochemistry' 227:334-341. (1995).
Request for Inter Partes Reexamination of U.S. Patent No. RE40,812 filed on Jun. 21, 2011 (Control No. 95/001,667) (20 pgs).
Decision granting Inter Partes Reexamination of of U.S. Patent No. RE40,812 (Control No. 95/001,667) mailed Sep. 8, 2011 (12 pgs).
Official Action issued in connection with U.S. Control No. 95/001,667 mailed Sep. 8, 2011 (15 pgs).
Supplemental Declaration of Professor Alexander M. Klibanov regarding invalidity of U.S. Patent No. 6,440,392 dated Apr. 22, 2009.
Supplemental Declaration of Professor Ashim K. Mitra regarding invalidity of U.S. Patent No. 6,440,392 dated Apr. 22, 2009.
Declaration of Professor Alexander M. Klibanov regarding invalidity of U.S. Patent No. 6,440,392 dated Oct. 14, 2008.
Petition under 37 CFR §§ 1.937 to Suspend Inter Partes Reexamination and Response to Sep. 8, 2011 Inter Partes Examination Office Action filed on Nov. 8, 2011 in U.S. Control No. 95/001,667 (74 pgs).
Petition under 37 CFR § 1.182 and 1.183 to Accept Response to Patent Owner's Petition and Response to Patent Owner's Petition in Inter Partes Reexamination of U.S. Patent No. RE40,812 filed on Nov. 18, 2011 in U.S. Control No. 95/001,667 (218 pgs).
Third Party Comments after Patent Owner Response in Inter Partes Reexamination of U.S. Patent No. RE 40,812 filed on Dec. 7, 2011 in U.S. Control No. 95,001,667 (30 pgs).
Submission Supplemental to the Response to Patent Owner's Petition in Inter Partes Reexamination of U.S. Patent No. RE40,812 filed on Jan. 9, 2012 in U.S. Control No. 95/001,667 (28 pgs).
Wade, A. et al., "Handbook of Pharmaceutical Excipients", eds. Second Edition, American Pharmaceutical Association, Washington, 1994, pp. 27-32, 35-37, 111-113, 123-125, 207-208, 267-268, 310-313, 340-343, 375-378, 441-414, 443-445, 526-528.
United States District Court, Chambers of Robert P. Patterson, Jr. District Judge; *Unigene Laboratories, et ano.* v. *Apox, Inc., et ano.*, Index No. 06 Civ. 5571 (RPP), Facsimile of Aug. 31, 2009 Opinion and Order Confirming Validity of U.S. Patent No, RE40,812 (30 pgs).
United States Court of Appeals for the Federal Circuit; *Unigene Laboratories, Inc. and Upsher-Smith Laboratories, Inc., Plaintiffs-Appellees,* v. *Apotex, Inc. and Apotex Corp.*, Defendants-Appellants; 2010-1006; Appeal from the United States District Court for the Southern District of New York in case No. 06-CV-5571, Judge Robert P. Patterson, Jr., Decided: Aug. 25, 2011, Confirming Validity of U.S. Patent No. RE40,812 (20 pgs).
In the Supreme Court of the United States; *Apotex Inc. and Apotex Corp., Petitioners* v. *Unigene Laboratories, Inc. and Upsher-Smith Laboratories, Inc.*, Respondents; On Petition for a Writ of Certiorari to the United States Court of Appeals for the Federal Circuit, Jan. 2012 (40 pgs).
In the Supreme Court of the United States; *Apotex, et al.* v. *Unigene Laboratories, et al.*, No. 11-879, Order Denying Apotex's Petition for a Writ of Certiorari on Mar. 19, 2012 (1 pg).

* cited by examiner

NASAL CALCITONIN FORMULATIONS

Matter enclosed in heavy brackets [ ] appears in the original patent but forms no part of this reissue specification; matter printed in italics indicates the additions made by reissue.

*Notice: More than one reissue application has been filed for the reissue of U.S. Pat. No. 6,440,392. The present reissue application is a continuation reissue application of parent reissue application Ser. No. 10/774,358 filed Feb. 5, 2004, now issued as Re. 40,812. Both the present reissue application and the parent reissue patent are reissues of U.S. Pat. No. 6,440,392.*

RELATED APPLICATIONS

This application is based upon and claims priority of U.S. Provisional Application No. 60/180,241, filed Feb. 4, 2000, which is hereby incorporated by reference.

BACKGROUND OF THE INVENTION

1. Field of the Invention

The present invention relates to [an] intranasal pharmaceutical compositions comprising calcitonin as an active ingredient and specific concentrations of citric acid or a salt thereof as a stabilizer and absorption enhancer.

2. Description of the Related Art

Calcitonins are a class of polypeptide hormones that are used in the treatment of a variety of conditions including osteoporosis, Paget's disease and malignant hypercalcemia. They are composed of amino acids and have been extracted from a number of sources including salmon, porcine, eel and human. Calcitonins with amino acid sequences identical to the natural forms have been produced by chemical synthesis as well as by recombinant technology.

Given their size and chemical composition, calcitonins were originally administered by subcutaneous or intramuscular injection. Other routes of administration were technically difficult because calcitonins were poorly absorbed through tissue and were readily degraded by bodily fluids. Despite these obstacles, a formulation (U.S. Pat. No. 5,759,565) was developed that could be administered via the nasal route. The nasal formulation was designed to be stored in a multi-dose container that was stable for an extended period of time and resisted bacterial contamination. The preservative in the formulation, benzalkonium chloride, was found to enhance the absorption of salmon calcitonin. However, benzalkonium chloride was reported (P. Graf et al., Clin. Exp. Allergy 25:395-400; 1995) to aggravate [rhintis] *rhinitis* medicamentosa in healthy volunteers who were given a decongestant nasal spray containing the preservative. It also had an adverse effect on nasal mucosa (H. Hallen et al., Clin. Exp. Allergy 25:401-405; 1995). Berg et al. (Laryngoscope 104:1153-1158; 1994) disclose that respiratory mucosal tissue that was exposed in vitro underwent severe morphological alterations. Benzalkonium chloride also caused significant slowing of the mucocilary transport velocity in the ex vivo frog palate test (P.C. Braga et al., J. Pharm. Pharmacol. 44:938-940; 1992).

SUMMARY OF THE INVENTION

Accordingly, the present invention provides a liquid pharmaceutical composition comprising calcitonin or an acid addition salt thereof and citric acid and/or salt thereof in a concentration from about 10 to about 50 mM, said composition being in a form suitable for nasal administration.

The present invention also provides a liquid pharmaceutical composition comprising about 2,200 MRC units of salmon calcitonin, about 10 mM citric acid, about 0.2% phenylethyl alcohol, about 0.5% benzyl alcohol, and about 0.1% TWEEN® 80.

The present invention further provides a liquid pharmaceutical composition comprising about 2,200 MRC units of salmon calcitonin, about 20 mM citric acid, about 0.2% phenylethyl alcohol, about 0.5% benzyl alcohol, and about 0.1% TWEEN® 80.

The present invention also provides a method of administering a calcitonin to a subject requiring calcitonin treatment, which method comprises administering via the nasal route to said subject a liquid pharmaceutical composition comprising calcitonin or an acid addition salt thereof and citric acid or salt thereof in a concentration from about 10 to about 50 mM.

The present invention further provides a method of improving the stability of a liquid pharmaceutical composition of calcitonin comprising adding citric acid or a salt thereof in a concentration from about 10 to about 50 mM to said composition.

The present invention also provides a method of improving the bioavailability or the concentration of plasma calcitonin in a subject following nasal administration of a liquid pharmaceutical composition of calcitonin, which method comprises adding citric acid or a salt thereof in a concentration from about 10 to about 50 mM to said composition prior to said administration.

DETAILED DESCRIPTION OF THE INVENTION

In accordance with the present invention it has now been surprisingly found that pharmaceutical compositions can be obtained comprising a calcitonin as active ingredient which meet the high standards of stability and bioavailability required for nasal application and which are, for example, eminently suitable for use in multiple dose nasal spray applicators, i.e., applicators capable of delivering a series of individual dosages over, e.g., period of several days or weeks, by the use of citric acid or a salt thereof in concentrations ranging from about 10 to about 50 mM as a buffering agent.

Surprisingly, it has also been found that use of citric acid or a salt thereof at increasing concentrations confers beneficial advantages in relation to the nasal absorption characteristics of calcitonin containing compositions and hence enhance calcitonin bioavailability levels consequential to nasal application. In addition, it has also been found that the use of citric acid or a salt thereof in concentrations ranging from about 10 to about 50 mM increase the stability of calcitonin containing compositions while at the same time higher concentrations of citric acid or salt thereof did not have the same stabilizing effect.

The calcitonins for use in the invention may be in free form or in pharmaceutically acceptable salt or complex form, e.g. in pharmaceutically acceptable acid addition salt form. Such salts and complexes are known and possess an equivalent degree of activity and tolerability to the free forms. Suitable acid addition salt forms for use in accordance with the invention include for example the hydrochlorides and acetates.

The above defined compositions may be applied in accordance with the invention to the nasal mucosa, e.g. either in drop or in spray form. As hereinafter described however, they are most preferably applied in spray form, i.e., in the form of finely divided droplets.

The compositions of the invention may of course also include additional ingredients, in particular components belonging to the class of conventional pharmaceutically applicable surfactants. In this connection it has in accordance with a further aspect of the present invention been found that the use of surface active agents generally in relation to the nasal application of calcitonins, in particular salmon calcitonin, may increase absorption via the nasal mucosa and hence improve obtained bioavailability rates.

Preferably, the liquid pharmaceutical calcitonin composition of the present invention contains a pharmaceutically acceptable, a liquid diluent or carrier suitable for application to the nasal mucosa, most preferably aqueous saline.

The compositions of the invention are formulated so as to permit administration via the nasal route. For this purpose they may also contain, e.g. minimum amounts of any additional ingredients or excipients desired, for example, additional preservatives or, e.g. ciliary stimulants such as caffeine.

Generally for nasal administration a mildly acid pH will be preferred. Preferably the compositions of the invention have a pH of from about 3 to 5, more preferably from about 3.5 to about 3.9 and most preferably 3.7. Adjustment of the pH is achieved by addition of an appropriate acid, such as hydrochloric acid.

The compositions of the invention should also possess an appropriate isotonicity and viscosity. Preferably they have an osmotic pressure of from about 260 to about 380 mOsm/liter. Desired viscosity for the nasal spray is preferably less than 0.98 cP. *In one embodiment, the osmotic pressure is from 250 to 350 mOsm/liter.*

Compositions in accordance with the present invention may also comprise a conventional surfactant, preferably a non-ionic surfactant.

When a surfactant is employed, the amount present in the compositions of the invention will vary depending on the particular surfactant chosen, the particular mode of administration (e.g. drop or spray) and the effect desired. In general, however, the amount present will be of the order of from about 0.1 mg/ml to about 10 mg/ml, preferably about 0.5 mg/ml to 5 mg/ml and most preferably about 1 mg/ml.

The amount of calcitonin to be administered in accordance with the method of the invention and hence the amount of active ingredient in the composition of the invention will, of course, depend on the particular calcitonin chosen, the condition to be treated, the desired frequency of administration and the effect desired.

As indicated in the following examples, bioavailability for calcitonins, in particular salmon calcitonin, as determined in terms of blood-plasma concentration following nasal administration in accordance with the teachings of the present invention has been found to be surprisingly high.

For nasal administration in accordance with the present invention, treatment will therefore suitably comprise administration of dosages of from about 50 to about 400 MRC units, more preferably from about 100 to about 200 MRC units at a frequency of from about once daily to about three times weekly. Conveniently dosages as aforesaid will be administered in a single application, i.e., treatment will comprise administration of single nasal dosages comprising about 50 to about 400 MRC units, preferably about 100 to about 200 MRC units, calcitonin. Alternatively such dosages may be split over a series of 2 to 4 applications taken at intervals during the day, the dosage at each application then comprising about 10 to about 200, preferably about 25 to about 100 MRC units.

The total composition quantity administered at each nasal application suitably comprises from about 0.05 to 0.15 ml, typically about 0.1 ml. Compositions for use in accordance with the invention accordingly suitably comprise from about 150 to about 8,000, preferably from about 500 to about 4,000, more preferably from about 500 to about 3,000, yet again more preferably from about 1,000 to about 2,500, and most preferably about 2,200 MRC units of calcitonin per ml.

For the purposes of nasal administration, the compositions of the invention will preferably be put up in a container provided with means enabling application of the contained composition to the nasal mucosa, e.g. put up in a nasal applicator device. Suitable applicators are known in the art and include those adapted for administration of liquid compositions to the nasal mucosa in drop or spray form. Since dosaging with calcitonins should be as accurately controlled as possible use of spray applicators for which the administered quantity is susceptible to precise regulation will generally be preferred. Suitable administrators include, e.g. atomizing devices, e.g. pump-atomizers and aerosol dispensers. In the latter case, the applicator will contain a composition in accordance with the invention together with a propellant medium suitable for use in a nasal applicator. The atomizing device will be provided with an appropriate spray adaptor allowing delivery of the contained composition to the nasal mucosa. Such devices are well known in the art.

The container, e.g. nasal applicator, may contain sufficient composition for a single nasal dosaging or for the supply of several sequential dosages, e.g. over a period of days or weeks. Quantities of individual dosages supplied will preferably be as hereinbefore defined. The stability of the compositions of the invention may be determined in conventional manner. As indicated hereinbelow, the calcitonin content of the compositions of the invention will degrade less than 50% in 15 days at 50° C. as indicated by standard analytical tests.

EXPERIMENTAL DESIGN—METHODS OF ADMINISTERING NASAL CALCITONIN AND MEASUREMENT OF PLASMA CONCENTRATION

Female Wistar rats, weighing between 225 and 250 g are anesthetized with a combination of ketamine and xyalzine, and a cannula is inserted into the carotid artery. The cannula is fitted to a three-way valve through which blood is sampled and replaced with physiological saline containing heparin. Formulated salmon calcitonin (sCT) (5 μg per 25 μl) is administered intranasally through a micropipette tip that was inserted 8 mm into the rat's nostril. For single-dose studies, 5 μg of sCT was administered. In multiple dose studies, sCT was administered four times in a volume of 25 μl each at 0, 30, 60 and 90 minutes for a total dose of 20 μg.

In single-dose studies, blood samples are collected prior to dosing and at 5, 15, 30, 60 and 120 minutes after dosing. In multiple-dose studies, blood samples are collected prior to dosing and at 30, 60, 90, 120 and 150 minutes after the administration of the first dose. Blood samples are always collected immediately before the administration of any additional [costs] *doses*.

Each sample (0.5 ml) of blood is collected into a heparinized 1 ml syringes and then transferred to chilled 1.5 ml polypropylene tubes containing 10 μl of heparin (500 U per ml). The tubes are centrifuged at approximately 3000 rpm for 20 minutes at 2-8° C. and the plasma supernatant is transferred to microcentrifuge tubes that were stored at −20° C. The concentration of sCT in plasma is determined by a competitive radioimmunoassay. Aliquots of the plasma samples and standards are incubated for 4 hours at room temperature with rabbit anti-sCT antibody. Subsequently, $^{125}$I-sCT is added and incubated overnight at 2-8° C. Antibody-bound $^{125}$I-sCT is isolated the next day by precipitating it with normal rabbit antiserum and goat anti-rabbit antibody. Radioactivity associated with the resulting pellets is measured with a gamma counter. The concentration of sCT in plasma is inversely proportional to the amount of radioactivity that was precipitated.

The values of Cmax are determined by inspection and the values for bioavailability (relative to an intravenous injection) are calculated from the areas under the curve that were obtained from plots of plasma sCT concentration as a function of time.

EXAMPLE 1

The following study examines the effect of the concentration of citric acid on the bioavailability and plasma concentration of nasally administered salmon calcitonin. Rats were administered intranasally as described previously 20 μl of rsCT (200 μg/ml) in 0.85% sodium chloride, 0.1% TWEEN® 80, 0.2% phenylethyl alcohol, 0.5% benzyl alcohol and varying amounts of citric acid adjusted to pH 3.7 at t=0, 20, 60 and 90 minutes. Samples of blood were taken prior to the administration of rsCT at these time points as well as at t=120 and 150 minutes. The resulting plasma samples were analyzed for rsCT by radioimmunoassay. Maximum rsCT levels were detected at t=120 minutes. The results of this study as shown in Table 1 indicate that the bioavailability and peak concentration of rsCT was a function of the concentration of citric acid in the formulation.

TABLE 1

EFFECT OF THE CONCENTRATION OF CITRIC ACID ON THE BIOAVAILABILITY AND PLASMA CONCENTRATION OF SALMON CALCITONIN ADMINISTERED INTRANASALLY TO RATS

| Citric acid (pH 3.7) | Bioavailability (percent ± sdev) | Maximum plasma sCT (ng/ml ± sdev) |
|---|---|---|
| 0 | 0.89 ± 0.19 | 1.10 ± 0.52 |
| 10 | 3.14 ± 1.77 | 3.66 ± 1.67 |
| 25 | 5.01 ± 2.34 | 5.11 ± 2.09 |
| 50 | 6.15 ± 1.31 | 6.05 ± 1.30 |
| 100 | 13.36 ± 3.38 | 12.98 ± 3.96 |

EXAMPLE 2

The following study examines the effect of different preservatives on the plasma concentration of nasally administered salmon calcitonin. Rats were administered intranasally as described previously 20 μl of sCT (200 μg/ml) in 0.85% sodium chloride, 0.1% TWEEN® 80 and a combination preservatives of either 0.2% phenylethyl alcohol and 0.5% benzyl alcohol or 0.27% methyl parabens and 0.04% propyl parabens at t=0, 30, 60 and 90 minutes. The results of this study as shown in Table 2 indicate that the bioavailability and peak concentration of rsCT are not significantly affected by the addition of the different preservatives.

TABLE 2

EFFECT OF PRESERVATIVES ON THE AVAILABILITY AND PLASMA CONCENTRATION OF SCT ADMINISTERED INTRANASALLY TO RATS

| Preservatives | Bioavailability (percent ± sdev) | Maximum plasma sCT (ng/m1 ± sdev) |
|---|---|---|
| None | 1.14 ± 0.87 | 1.24 ± 0.79 |
| 0.2% phenylethyl alcohol - 0.5% benzyl alcohol | 0.89 ± 0.19 | 1.10 ± 0.52 |
| 0.27 methyl parabens - 0.04% propyl parabens | 1.08 ± 0.86 | 1.47 ± 1.46 |

EXAMPLE 3

The following study examines the effect of the concentration of citric acid on the stability of salmon calcitonin stored for varying periods at a temperature of 50° C. Nasal formulations containing sCT (200 μg/ml), 0.25% phenylethyl alcohol, 0.5% benzyl alcohol and 0.1% TWEEN® 80 were adjusted to pH 3.7 with either HCl or the indicated amount of buffered citric acid. The formulations were stored at 50° C. in sealed glass containers for the indicated amount of time and analyzed for sCT by high performance liquid chromatography. The results as shown in Table 3 indicate that in the absence of citric acid, the amount sCT in the formulation decreased steadily between 0 and 9 days after the study was begun. In the presence of citric acid (10-50 mM) the rate of disappearance of sCT decreased significantly. However, as the concentration of citric acid was further increased, the rate of sCT disappearance from vials stored at 50° C. increased in proportion to the amount of buffered citric acid in the formulation.

TABLE 3

EFFECT OF THE CONCENTRATION OF CITRIC ACID ON THE STABILITY OF sCT STORED FOR VARYING PERIODS AT 50° C.

| Citric Acid (pH 3.7) | 0 mM | 10 mM | 20 mM | 50 mM | 100 mM |
|---|---|---|---|---|---|
| | Percent sCT Recovered | | | | |
| Days at 50° C. | | | | | |
| 0 | 100 | 100 | 100 | 100 | 100 |
| 3 | 83 | 94 | 91 | 90 | 87 |
| 6 | 53 | 90 | 87 | 83 | 77 |
| 9 | 24 | 82 | 78 | 73 | 66 |
| 15 | 22 | 74 | 68 | 61 | 20 |

What is claimed is:

[1. A liquid pharmaceutical composition comprising calcitonin or an acid addition salt thereof and citric acid and/or salt thereof in a concentration from 10 to about 50 mM, said composition being in a form suitable for nasal administration.]

[2. The liquid pharmaceutical composition of claim 1 further comprising a pharmaceutically acceptable, aqueous liquid nasal carrier.]

[3. The liquid pharmaceutical composition of claim 2, wherein said carrier comprises aqueous saline.]

[4. The liquid pharmaceutical composition of claim 1, wherein said composition is in the form of a nasal spray.]

[5. The liquid pharmaceutical composition of claim 4 having a viscosity of less than 0.98 cP.]

[6. The liquid pharmaceutical composition of claim 1, wherein the calcitonin is selected from the group consisting of salmon calcitonin, human calcitonin, porcine calcitonin and 1,7-Asu-eel calcitonin.]

[7. The liquid pharmaceutical composition of claim 1, wherein the calcitonin is salmon calcitonin.]

[8. The liquid pharmaceutical composition of claim 1, wherein said calcitonin, or salt is present in an amount of from about 100 to about 8,000 MRC units/ml.]

[9. The liquid pharmaceutical composition of claim 1, wherein said calcitonin, or salt is present in an amount of from about 500 to about 4,000 MRC units/ml.]

[10. The liquid pharmaceutical composition of claim 1, wherein said calcitonin, or salt is present in an amount of from about 500 to about 3,000 MRC units/ml.]

[11. The liquid pharmaceutical composition of claim 1, wherein said calcitonin, or salt is present in an amount of from about 1,000 to about 2,500 MRC units/ml.]

[12. The liquid pharmaceutical composition of claim 1 having a pH of from about 3 to about 5. ]

[13. The liquid pharmaceutical composition of claim 1 having a pH of from about 3.5 to about 3.9.]

[14. The liquid pharmaceutical composition of claim 1 having a pH of about 3.7.]

15. [The liquid pharmaceutical composition of claim 1] *A liquid pharmaceutical composition comprising calcitonin or an acid addition salt thereof and a bioavailability enhancing agent selected from the group consisting of citric acid, citric acid salt and a combination thereof, wherein the combined concentration of all bioavailability enhancing agents is 10-25 mM, said composition being in a form suitable for nasal administration and* having an osmotic pressure of from [about] 250 to [about] 350 mOsm/liter, *wherein said citric acid or citric acid salt concentration is 20 mM, and wherein the pH of the composition is from 3.5 to 3.9.*

[16. The liquid pharmaceutical composition of claim 1 further containing at least 0.1% by weight of polyoxyethylene (20) sorbitan monooleate.]

[17. The liquid pharmaceutical composition of claim 1 further containing at least one preservative selected from the group consisting of benzyl alcohol, phenylethyl alcohol, methyl parabens, ethyl parabens, propyl parabens and butyl parabens.]

[18. A liquid pharmaceutical composition comprising about 2,200 MRC units of salmon calcitonin, about 10 mM citric acid, about 0.2% phenylethyl alcohol, about 0.5% benzyl alcohol, and about 0.1% polyoxyethylene(20) sorbitan monooleate.]

[19. A liquid pharmaceutical composition comprising about 2,200 MIC units of salmon calcitonin, about 20 mM citric acid, about 0.2% phenylethyl alcohol, about 0.5% benzyl alcohol, and about 0.1% polyoxyethylene(20) sorbitan monooleate.]

20. A method of administering a calcitonin to a subject requiring calcitonin treatment, which method comprises administering to said subject [a composition as defined in claim 1] via the nasal route *a liquid pharmaceutical composition for nasal administration comprising calcitonin or an acid addition salt thereof and a bioavailability enhancing agent selected from the group consisting of citric acid, citric acid salt and a combination thereof, wherein the combined concentration of all bioavailability enhancing agents is 10-25 mM, said composition having a pH of from 3.5-3.9.*

21. The method of claim 20, wherein the amount of calcitonin administered is from about 200 to about 600 MRC units.

[22. A method of improving the stability of a liquid pharmaceutical composition of calcitonin comprising adding citric acid or a salt thereof in a concentration from 10 to about 50 mM to said composition.]

[23. A method of improving the bioavailability or the concentration of plasma calcitonin in a subject following nasal administration of a liquid pharmaceutical composition of calcitonin, which method comprises adding citric acid or a salt thereof in a concentration from 10 to about 50 mM to said composition prior to said administration.]

*24. The pharmaceutical composition of claim 15, wherein said composition includes aqueous saline.*

*25. The pharmaceutical composition of claim 15, wherein said composition has a viscosity of less than 0.98 cP.*

*26. The pharmaceutical composition of claim 15, wherein said composition further contains at least 0.1% by weight of polyoxyethylene(20) sorbitan monooleate.*

*27. The pharmaceutical composition of claim 15, wherein said composition further contains at least one preservative selected from the group consisting of benzyl alcohol, phenylethyl alcohol, methyl parabens, ethyl parabens, propyl parabens and butyl parabens.*

*28. The pharmaceutical composition of claim 15, wherein said calcitonin is salmon calcitonin.*

*29. A method of administering a calcitonin to a subject requiring calcitonin treatment, said method comprising nasally administering to said subject a therapeutically effective amount of the composition of claim 15.*

*30. The method of claim 20 wherein the calcitonin is salmon calcitonin.*

*31. An aqueous pharmaceutical composition for nasal delivery comprising salmon calcitonin or an acid addition salt thereof, a bioavailability enhancing agent selected from the group consisting of citric acid, citric acid salt and a combination thereof, wherein the combined concentration of all said bioavailability enhancing agents is 10-50 mM, said composition having a pH of from 3.5-3.9, and an osmotic pressure from 250 to 350 mOsm/liter.*

*32. The pharmaceutical composition of claim 31, further containing at least one preservative selected from the group consisting of benzyl alcohol, phenylethyl alcohol, methyl parabens, ethyl parabens, propyl parabens and butyl parabens.*

*33. The pharmaceutical composition of claim 31, wherein combined concentration of all said bioavailability enhancing agents is 20 mM.*

*34. The pharmaceutical composition of claim 33, further comprising 0.2% phenylethyl alcohol, 0.5% benzyl alcohol and 0.1% polyoxyethylene (20) sorbitan monooleate.*

*35. A method of administering a calcitonin to a subject requiring calcitonin treatment, said method comprising nasally administering to said subject a therapeutically effective amount of the composition of claim 31.*

*36. A method of administering a calcitonin to a subject requiring calcitonin treatment, said method comprising nasally administering to said subject a therapeutically effective amount of the composition of claim 34.*

* * * * *